United States Patent
Fujii et al.

[11] Patent Number: 5,961,473
[45] Date of Patent: Oct. 5, 1999

[54] HOLDER FOR A BLOOD COLLECTION NEEDLE

[75] Inventors: Tsuguo Fujii, Ootsu; Keizo Matsumura, Ibaragi; Toshihiro Kikuchi, Osaka, all of Japan

[73] Assignee: Nissho Corporation, Osaka, Japan

[21] Appl. No.: 09/045,714

[22] Filed: Mar. 23, 1998

Related U.S. Application Data

[62] Division of application No. 08/728,146, Oct. 9, 1996, Pat. No. 5,797,490.

[30] Foreign Application Priority Data

Nov. 22, 1995 [JP] Japan .................................. 7-304855

[51] Int. Cl.⁶ .................................................. A61B 10/00
[52] U.S. Cl. ............................................ 600/576; 604/192
[58] Field of Search .............................. 600/576; 604/192

[56] References Cited

U.S. PATENT DOCUMENTS

| | | | |
|---|---|---|---|
| 3,595,086 | 7/1971 | Bonnet et al. ....................... | 73/864.01 |
| 4,942,881 | 7/1990 | Al-Sioufi et al. ..................... | 128/763 |
| 5,020,665 | 6/1991 | Bruno ................................... | 206/366 |
| 5,125,414 | 6/1992 | Dysarz ................................. | 600/576 |
| 5,127,531 | 7/1992 | Onodera ............................... | 211/74 |
| 5,401,250 | 3/1995 | Shields ................................. | 604/192 |
| 5,509,319 | 4/1996 | Hitzman ............................... | 73/864.14 |

FOREIGN PATENT DOCUMENTS 62-148646 7/1987 Japan .
WO 89/05118 6/1989 WIPO .

*Primary Examiner*—Cary O'Connor
*Assistant Examiner*—Pamela S. Wingood
*Attorney, Agent, or Firm*—Kubovcik & Kubovcik

[57] ABSTRACT

A holder for a blood collection needle includes a cylinder and a needle fixing mechanism disposed at a distal end wall of the cylinder. The needle fixing mechanism includes a first slider, a second slider, a retainer, and a frame. The first slider and the retainer have half female members integrally formed thereon. The first slider is movable toward the second slider such that the mechanism is in a closed state in which the first slider engages the frame such that the half female members come together to define a complete female member. The second slider is movable toward the first slider such that the mechanism is in an open state in which the first slider is disengaged from the frame. The frame is affixed to the cylinder so as to hold the first slider, the second slider, and the retainer on the end wall thereof.

1 Claim, 7 Drawing Sheets

HOLDER FOR A BLOOD COLLECTION NEEDLE

This application is a divisional application of Ser. No. 08/728,146, filed Oct. 9, 1996, now U.S. Pat. No. 5,797,490.

BACKGROUND OF THE INVENTION

1. Field of the Invention

The present invention relates to a holder for a blood collection needle and, more particularly, to a holder that includes a means for securing a blood collection needle and a further means for retaining a blood collection tube such that the needle can be used together with the tube when a blood sample is taken from a human body for the purpose of blood analysis such as blood sedimentation.

2. Prior Art

Generally, the prior art blood collection needles have male-threaded hubs which are screwed into female-threaded needle holders. The needles can be unscrewed by hand for removal from the holders, after fitting a protector on each needle through which a blood sample has been taken. Physicians and medical workers have erroneously and accidentally pricked their palms or fingers when attaching those protectors to such used needles. As a result, some physicians and medical workers have been infected with serious diseases including AIDS viruses and hepatitis viruses. Therefore, certain proposals have been made to make it unnecessary for physicians to touch the used needles when removing and discarding them from the holders. Such proposals of the so-called "one-touch holder" are disclosed in Japanese Patent Publication No. 1-28589 and Japanese Unexamined Patent Publication No. 2-297342 (corresponding to U.S. Pat. No. 5,069,225).

A fastener combined with a needle seat included in the holder shown in Japanese Patent Publication No. 1-28589 includes a spring for urging an improved blood collection needle toward the seat. The improved needle has an indented hub to be releasably fixed on the seat. A pair of hub support walls shown in Japanese Unexamined Patent Publication No. 2-297342 are elastically expansible to grip a proximal portion of the hub. This hub secured to the blood collection needle also has a lug or recess engageable with the support walls.

One-touch type holders, however, are applicable only to the needle hubs having a special indent or lug not found in the usual holders. In other words, ordinary blood collection needles cannot necessarily be used with such holders. Further, such holders, because they are of the non-screwing type, sometimes fail to hold the needle firmly and rigidly.

SUMMARY OF THE INVENTION

An object of the present invention is therefore to provide a holder for a blood collection needle, which holder can firmly hold the needle even if it has a threaded hub.

In order to achieve the object, the holder for a blood collection needle includes a cylinder and a needle fixing mechanism. The cylinder has an open proximal end, a distal end closed by an end wall, and an aperture formed in the end wall. The needle fixing mechanism, which is disposed at the distal end of the cylinder, includes two sliders which are movable toward each other along the end wall. When the first slider is moved toward the second slider along the end wall, the mechanism is brought into a closed state. When the second slider is moved toward the first slider along the end wall, the mechanism is brought into an open state.

In a preferred embodiment, the needle fixing mechanism includes a first slider having a half female member integrally formed thereon, a retainer having a half female member integrally formed thereon, a second slider formed such that the first slider does not slip off the cylinder, and a frame for holding the first and second sliders and the retainer on the end wall of the cylinder. When the first slider is moved toward the second slider the half female members come together to define a complete female member and the first slider is in engagement with the frame. When the second slider is moved toward the first slider, the first slider is in disengagement with the frame.

In this embodiment, the holder may be designed such that the second slider protrudes from the frame when the first slider is in engagement with the frame, and the first slider protrudes from the frame when disengaged therefrom. And the first slider is movable toward the second slider to engage with the frame, and the second slider is movable toward the first slider to disengage from the frame. To facilitate removal of the blood collection needle from the holder, a lug is integrally formed on the second slider, and the retainer has an opening through which the lug passes. The lug pushes the needle hub sideways and thereby facilitates easy removal of the needle from the holder.

To prevent the second slider from being erroneously or accidentally pushed, which would cause the blood connection needle to be dislodged from the holder, the second slider may be designed so as not to protrude from the frame when the first slider engages with the frame. In this case, the first slider protrudes from the frame when disengaged therefrom. To further prevent the second slider from being erroneously or accidently pushed, the second slider may be colored to distinguish it from the first slider. This helps minimize the likelihood that the second slider is oriented so that it is accidentally pressed by the skin, which can result in untimely release of the needle.

DETAILED DESCRIPTION OF THE PREFERRED EMBODIMENTS

Figure 1:
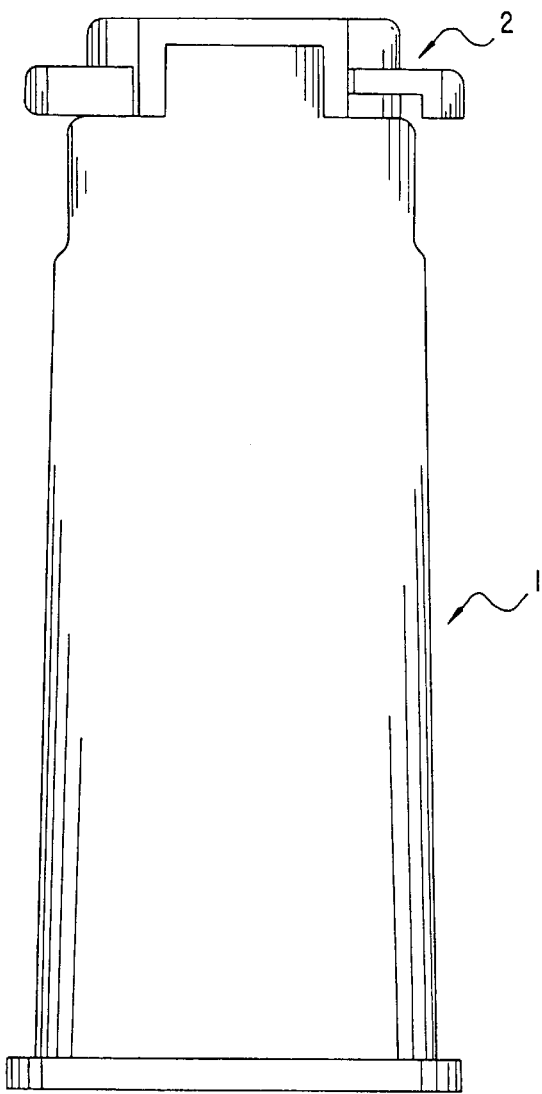
FIG. 1 is a side view of a holder for a blood collection needle provided in an embodiment of the present invention.
Figure 2:
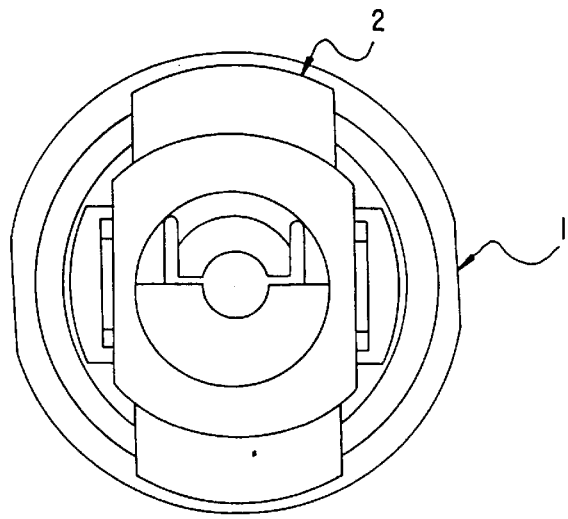
FIG. 2 is a plan view of the holder shown in FIG. 1.

As shown in FIGS. 1 and 2, the holder for a blood collection needle includes cylinder 1 and needle fixing mechanism 2. The mechanism 2 includes two sliders: first slider 22 and second slider 23. Sliders 22 and 23 are movable or slidable along end wall 11 (shown in detail in FIG. 6) of cylinder 1. When one of the sliders, e.g., first slider 22, is moved toward the other slider, e.g., second slider 23, mechanism 2 is brought into a closed state. In this closed state, mechanism 2 can securely hold a needle by, for example, engaging a male member integral with a hub formed on the needle. On the other hand, when the situation is reversed, e.g., second slider 23 is moved toward first slider 22, mechanism 2 is brought into an open state. In this open state, a needle can be removed from mechanism 2.

The holder outlined above will be described in detail referring to FIGS. 3 to 19.

Figure 6:
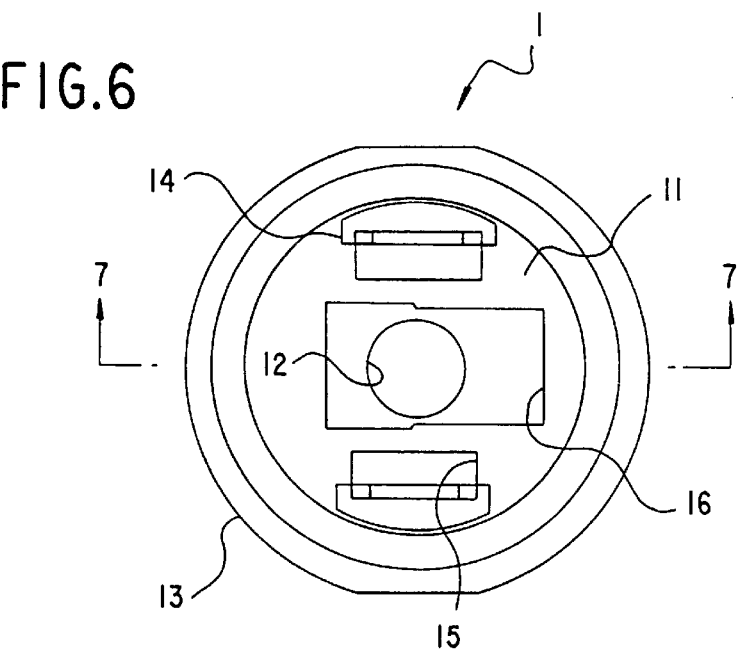
FIG. 6 is a plan view of a cylinder included in the holder shown in FIG. 1.
Figure 7:
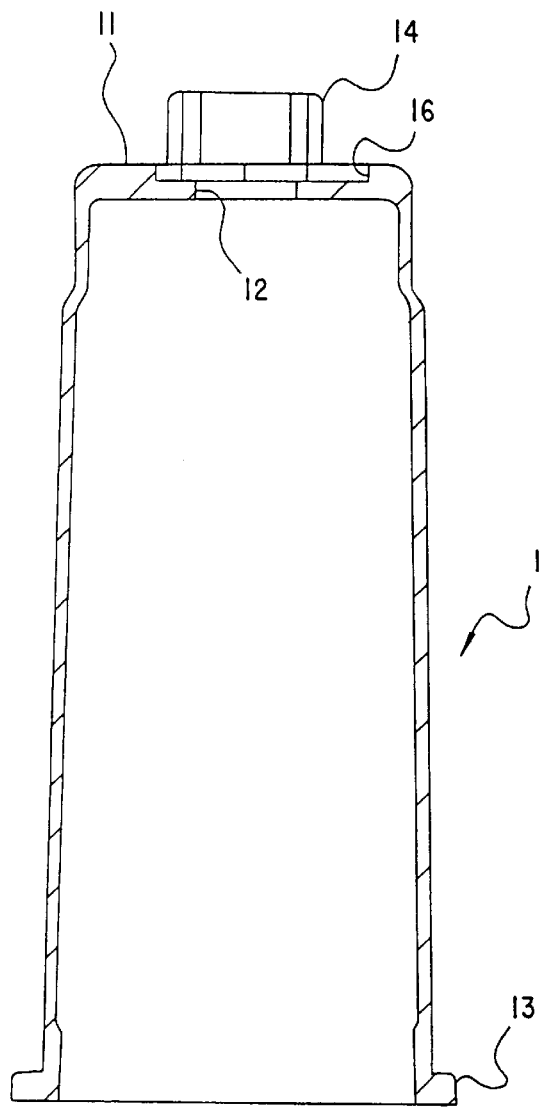
FIG. 7 is a cross section taken along the line 7—7 in FIG. 6.

As shown in FIGS. 6 and 7, cylinder 1 has a distal end closed with end wall 11, and an open proximal end. Central aperture 12 and a pair of side openings 15 are formed in the end wall 11 of cylinder 1. Side openings 15 are used to hold needle fixing mechanism 2. Central aperture 12 is of such a size that a cannula of the blood collection needle covered with a rubber sheath can be inserted into central aperture 12. A rear side of the needle carried by mechanism 2 juts into the interior of cylinder 1 so that when a blood collection tube (not shown) is inserted therein from the open proximal end thereof a rubber stopper of the tube is pierced by the needle. Side openings 15 are of such a size as to receive therethrough the respective feet 241 of a frame detailed below. Longer sides of each opening 15 are slightly longer than the width of feet 241. Shorter sides of each of the openings 15 are also slightly longer than the thickness of hook 242 formed at an end of each foot 241. Cylinder 1 is tapered to reduce its diameter toward the distal end. It is preferred that cylinder 1 has at its proximal end a flange 13 formed integral therewith to make it easier to grip the cylinder 1. A pair of guide fences 14 protrude from the cylinder's distal end, for ease of attaching thereto needle fixing mechanism 2. Bottom 211 of retainer 21 (described later) fits in recess 16 formed in end wall 11, together with bottom 222 of engageable portion 221 of first slider 22. A portion of recess 16 for receiving bottom 222 has a width slightly smaller than another portion for the other bottom 211.

The needle fixing mechanism 2 is attached to an outer face of the cylinder's end wall 11, between and in parallel with guide fences 14. The needle fixing mechanism 2 includes four parts: retainer 21, first slider 22, second slider 23, and frame 24. As can best be seen in FIGS. 3 and 5, retainer 21 and first slider 22 have half female members 213 and 223, respectively, formed integral therewith. In their "closed" position, half female members 213 and 223 firmly hold the needle on mechanism 2. The half female members 213 and 223 can also be spaced apart from each other to take their "open" position shown in FIG. 4, when first slider 22 slides away from retainer 21 so as to release the needle.

Figure 3:
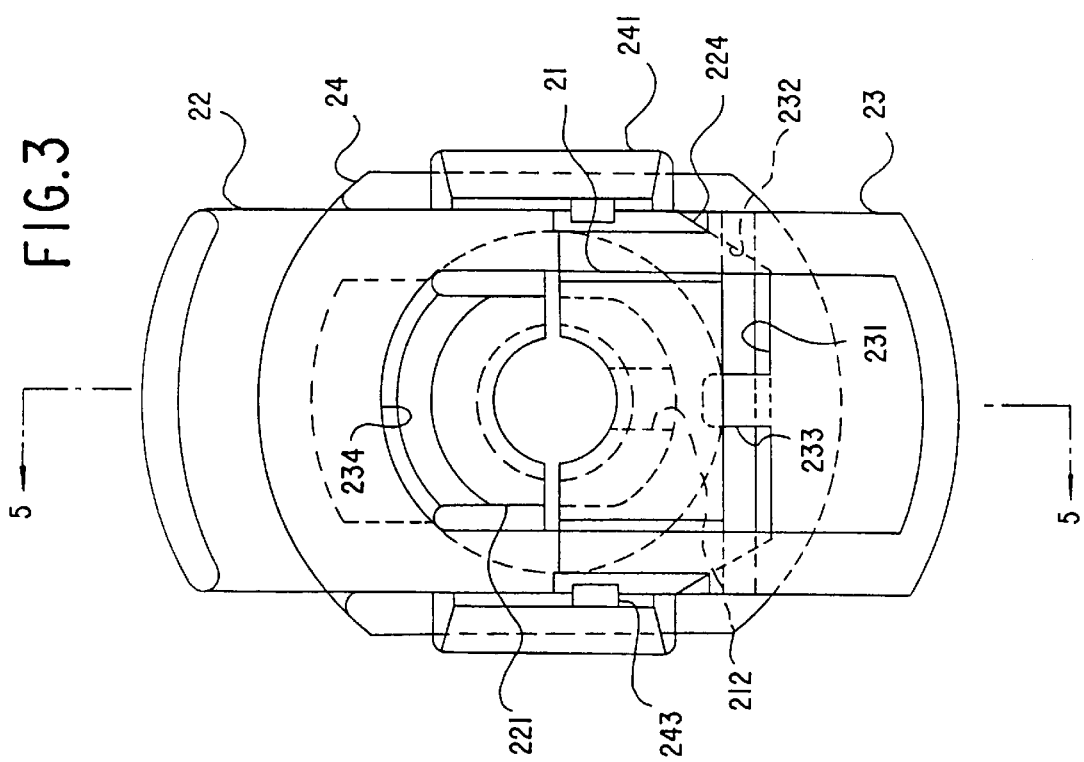
FIG. 3 is a bottom view of a needle fixing mechanism included in the holder and shown in one position fixing the needle thereon, wherein the mechanism includes a retainer, a first slider, a second slider, and a frame.
Figure 5:
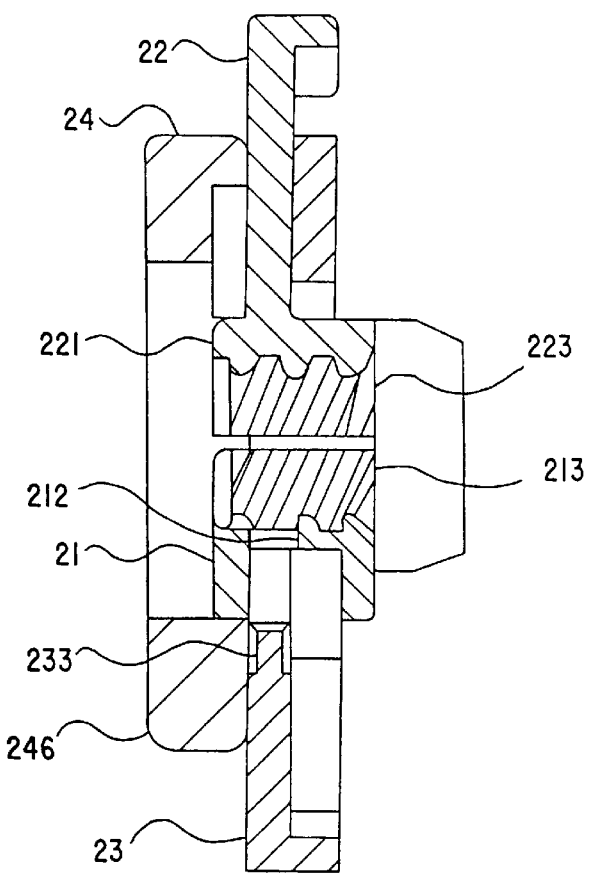
FIG. 5 is a cross section taken along the line 5—5 in FIG. 3.

The four parts described above as making up needle fixing mechanism 2 are arranged relative to each other in the manner shown in FIGS. 3 and 5. Such an arrangement enables first slider 22 to slide toward retainer 21 and engage with frame 24, thereby causing their half female members 213 and 223 to come together to form a complete female member. In detail, grooves 244 and 245 are formed in the lower surface of ceiling 246, which is a major flat portion of frame 24. Retainer 21 and first slider 22, which fit in grooves 244 and 245, respectively, have their upper surfaces in contact with the ceiling's lower surface. Second slider 23 set on retainer 21 and first slider 22 has a cavity 231 which accommodates the retainer 21 together with the first slider's engageable portion 221. Frame 24 carrying the mechanism 2 in the described manner will be secured to the outer face of the cylinder's end wall 11, to thereby provide the blood collection needle holder.

In the "closed" position referred to above, in which first slider 22 having hooks 224 and frame 24 having guide walls 248 engage with each other, grooves 225 of the hooks 224 serve to grip firmly protrusions 243 of the guide walls 248. Thus, first slider 22 is inhibited from moving away from retainer 21. Second slider 23 has releasers 232 formed integral therewith. Slanted ends of the releasers 232 are located adjacent to or in contact with slanted ends 226 of hooks 224, in the "closed" state of the mechanism 2. Also in this "closed" state, hub pushing lug 233 of second slider 23 is exposed from opening 212 through which it has passed.

Figure 4:
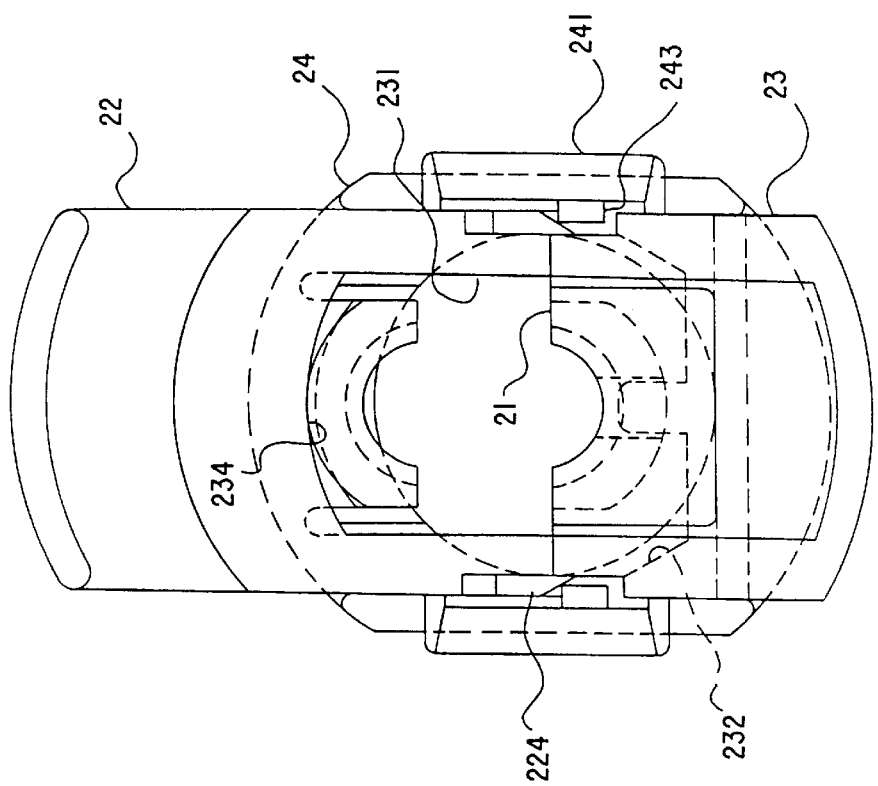
FIG. 4 is a bottom view of the needle fixing mechanism shown in another position allowing the needle to be dismounted.

In the "open" state the four parts of needle fixing mechanism 2 take their position as shown in FIG. 4. The half female members 213 and 223 of retainer 21 and first slider 22, respectively, are spread apart from each other such that the blood collection needle is not firmly held. Grooves 225 in hooks 224 of first slider 22 are not in engagement with protrusions 243 of guide walls 248 of frame 24. Thus, in such an "open" position first slider 22 can slide toward retainer 21. Also in the "open" state, releasers 232, which are part of second slider 23, have their ends in contact with or close to protrusions 243 of guide walls 248. The hub pushing lug 233 of second slider 23 will have passed the retainer's opening 212 so as to protrude a small distance from the retainer's half female member 213.

Figure 8:
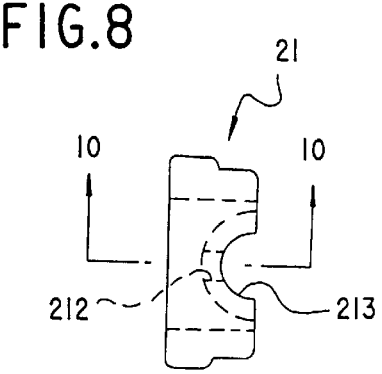
FIG. 8 is a plan view of the retainer shown in FIG. 3.
Figure 10:
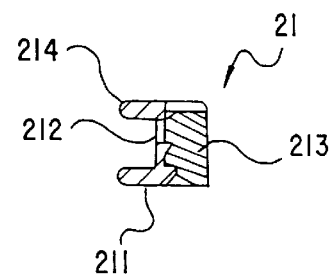
FIG. 10 is a cross section taken along the line 10—10 in FIG. 8.
Figure 9:
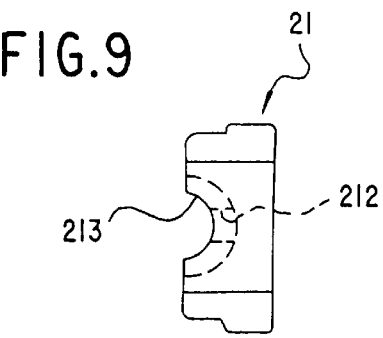
FIG. 9 is a bottom view of the retainer.

As described above, retainer 21 includes half female member 213 shown in FIGS. 8 to 10 (member 213 being screw-threaded in the illustrated embodiment) and is fixed on frame 24. Bottom face 211 of retainer 21 is broader than its upper face 214, and the opening 212 for passing hub pushing lug 233 of second slider 23 penetrates the portion of the retainer 21 adjacent to upper face 214. When assembling needle fixing mechanism 2, first slider 22 is disposed on the retainer 21 in such a manner that the former's hooks 224 rest on the latter's bottom face 211.

Figure 11:
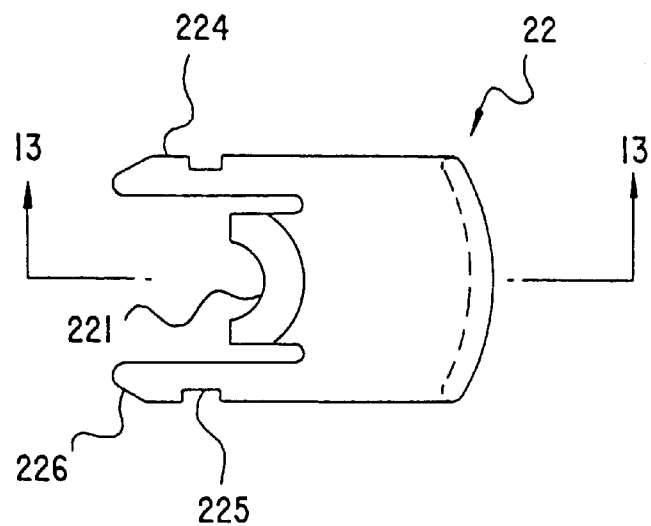
FIG. 11 is a plan view of the first slider shown in FIG. 3.
Figure 13:
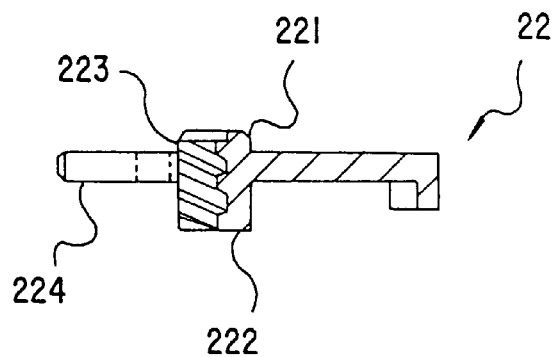
FIG. 13 is a cross section taken along the line 13—13 in FIG. 11.
Figure 12:
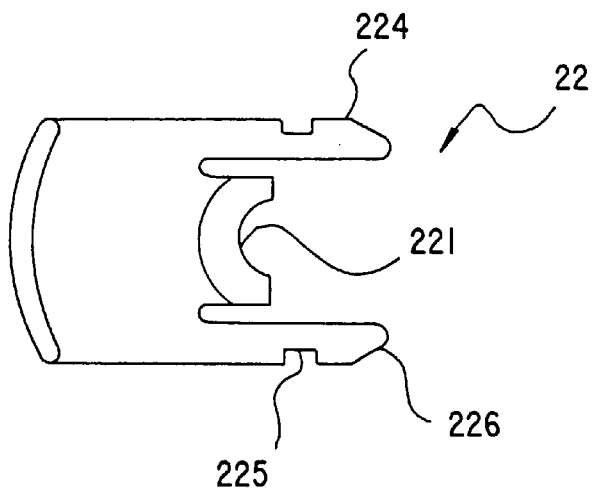
FIG. 12 is a bottom view of the first slider.
Figure 14:
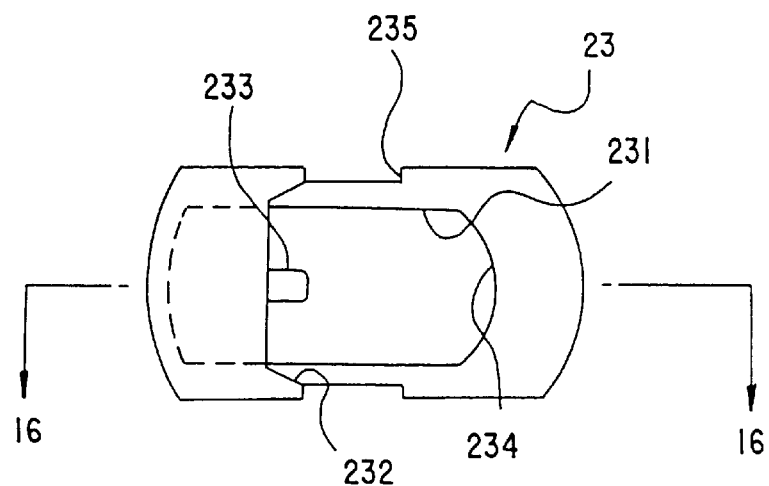
FIG. 14 is a plan view of the second slider shown in FIG. 3.
Figure 16:
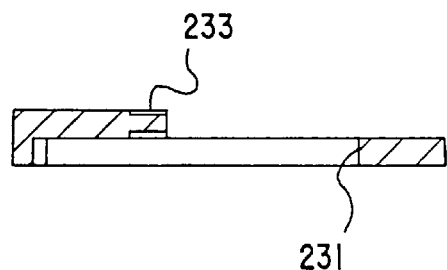
FIG. 16 is a cross section taken along the line 16—16 in FIG. 14.
Figure 15:
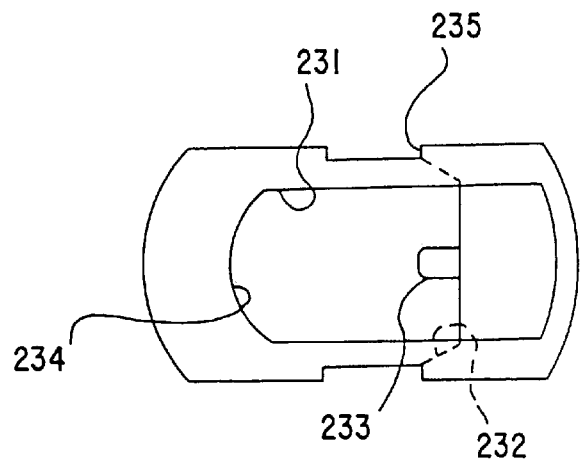
FIG. 15 is a bottom view of the second slider.
Figure 17:
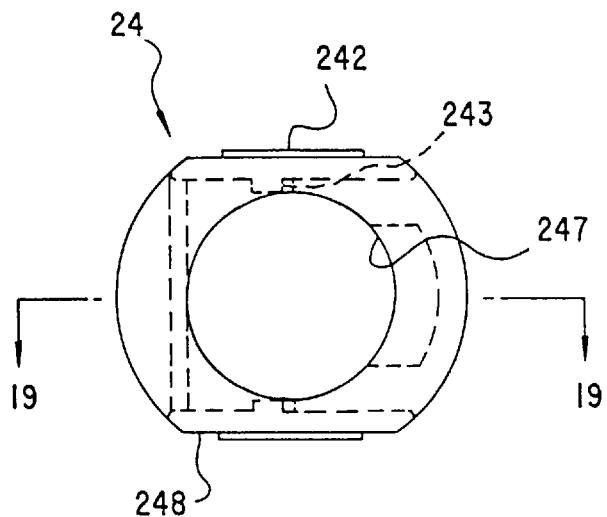
FIG. 17 is a plan view of the frame shown in FIG. 3.
Figure 19:
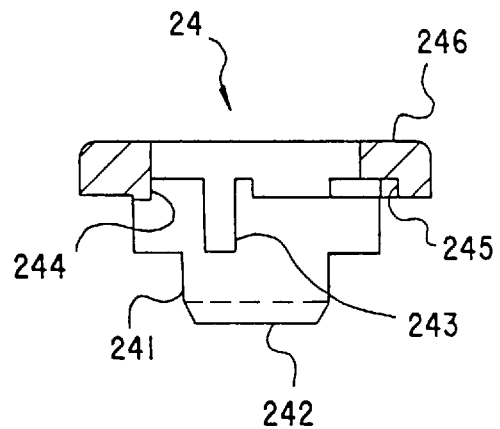
FIG. 19 is a cross section taken along the line 19—19 in FIG. 17.
Figure 18:
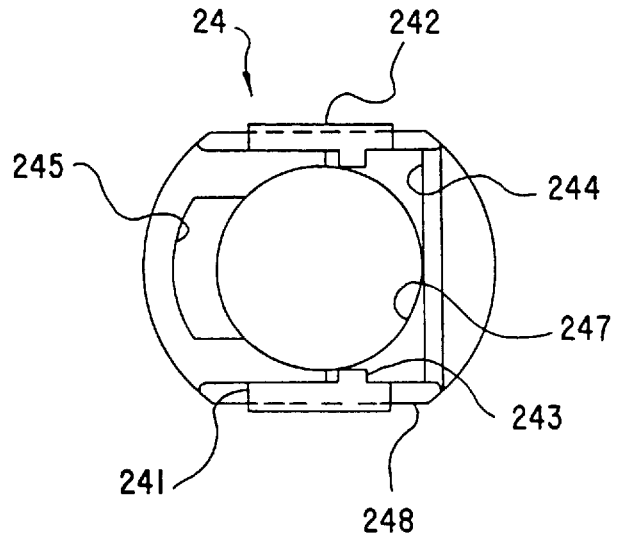
FIG. 18 is a bottom view of the frame.

Also as described above, first slider 22 includes engageable portion 221 having half female member 223 shown in FIGS. 11 to 13 (member 223 being screw-threaded in the illustrated embodiment), in addition to hooks 224. And first slider 22 is slidable along guide walls 248 formed upright on frame 24. Hooks 224 as locking members include a pair of arms extending in parallel with each other from outer sides of engageable portion 221. Grooves 225 mating the frame's protrusions 243 are formed in outer sides of hooks 224, and slanted ends 226 extending from the portions where grooves 225 are formed are tapered to reduce their width toward their extremities. The tapered surface of each slanted end 226 extends in parallel with each corresponding releaser 232 of second slider 23, whereby hooks 224 can flex inward when each slanted end 226 is pushed by releasers 232 so as to release protrusions 243 from grooves 225.

As described above, second slider 23 has cavity 231 defined in part between stopping dike 234, which prevents first slider 22 from slipping off frame 24, and a counter wall facing same. Hub pushing lug 233 juts from the counter wall so as to pass through the retainer's opening 212. As noted above, releasers 232 disposed outside the cavity 231 serve to disengage the frame's protrusions 243 from the grooves 225 of the first slider's hooks 224. Similar to first slider 22, second slider 23 is also slidable along and between the frame's guide walls 248. A pair of cutouts 235 formed in the outer surfaces of the side walls between which the cavity 231 is defined has facing shoulders, which alternately abut against protrusions 243 so as to restrict the range of the longitudinal stroke of second slider 23.

Frame 24 acts as a base for holding retainer 21, first slider 22, and second slider 23 on cylinder 1. Bore 247 in frame 24 is larger than the full female member composed of the half female members 213 and 223 that are respectively integral with retainer 21 and the first slider's engageable portion 221. Feet 241 of frame 24 extend downward from guide walls 248 (for guiding sliders 22 and 23) so as to secure needle fixing mechanism 2 to cylinder 1. Protrusions 243 engageable with the hooks' grooves 225 of first slider 22 are formed on inner faces of feet 241. The further hooks 242 protruding outward from lower end portions of feet 241 serve to secure frame 24 on cylinder 1. Recesses 244 and 245 formed in the lower face of frame 24 are configured to receive and hold retainer 21 and first slider 22, respectively.

Although FIGS. 3–5 show that both sliders 22 and 23 jut sideways from cylinder 1 in the embodiment, those skilled in the art will recognize that the holder may be modified such that only one slider juts sideways from the cylinder. For example, the distance between engageable portion 221 and an end facing same may be shortened in first slider 22 shown in FIGS. 11–13, with the distance across cavity 231 formed between stopping dike 234 and a portion facing same of second slider 23 shown in FIGS. 14–16 also being reduced. In such a modified holder, only second slider 23 will protrude sideways in the "closed" state, while only first slider 22 will do so in the "open" state. Thus, the release of the blood collection needle from mechanism 2 can be carried out more simply by pressing the one protruding slider (i.e., second slider 23).

The holder also may be modified such that second slider 23 does not jut sideways from cylinder 1. For example, the distance between engageable portion 221 and an end facing same may be shortened in first slider 22 shown in FIGS. 11–13, with the distance across cavity 231 formed between stopping dike 234 and a portion facing same of second slider 23 shown in FIGS. 14–16 being reduced more than the case in which only one of sliders 22 and 23 juts sideways from cylinder 1. In such a modified holder, neither slider 22 nor slider 23 will protrude sideways in the "closed" state, while only first slider 22 will do so in the "open" state. In this case, it is preferred that second slider 23 be colored, because it is difficult to distinguish between first slider 22 and second slider 23. Thus, the release of the blood collection needle from mechanism 2 can be carried out by pressing the colored slider (i.e., second slider 23). The advantage of coloring slider 23 is that it may prevent second slider 23 from being oriented so that it is accidently pressed by the skin, which can result in untimely release of the needle.

Needle fixing mechanism 2 may be manufactured using any suitable material. First slider 22 and frame 24 have flexible hooks 224 and 242, respectively, so that they should be made of a flexible resin such as polyethylene, polypropylene, polyester, or an ABS resin. Retainer 21 and second slider 23 may be made of any suitable material including flexible resins, metals, and non-flexible resins.

Those skilled in the art will recognize that needle fixing mechanism 2 is not necessarily restricted to the structure described herein, but may be modified with respect to its structure, the number of parts, and the shapes thereof, insofar as at least two sliders are employed to cooperate with each other. For example, those skilled in the art will recognize that first slider 22 may be caused to engage with and disengage from frame 24 in a manner different from that shown in the described embodiment. In one modification, the first slider's hooks 224 may have protrusions engageable with grooves or apertures formed in frame 24, so that they are disengaged from each other by using releaser 232 of second slider 23 as in the described embodiment.

In operation, the parts described above will function to hold and release the blood collection needle in the manner shown in FIGS. 3 to 5.

In FIGS. 3 and 5, half female member 223 of the first slider's engageable portion 221 is positioned adjacent to half female member 213 of retainer 21, with grooves 225 of the first slider's hooks 224 being in engagement with protrusions 243 of frame 24. In this state in which first slider 22 cannot move longitudinally thereof, half female members 213 and 223 form a stable and full female member engaging with the needle.

After the needle thus firmly held on mechanism 2 is used to collect a blood sample, second slider 23 will be pushed toward first slider 22. Consequently, slanted releasers 232 of second slider 23 will be forced to advance along and urge inward slanted ends 226 of the first slider's hooks 224. Hooks 224 thus elastically bend to an extent such that their grooves 225 disengage from the protrusions 243 of frame 24. At the same time, releasers 232 will push hooks 224 so that first slider 22 is driven away from the retainer 21 and half female members 213 and 223 are spaced apart from each other as shown in FIG. 4. As it is possible that the needle hub would stick to the screwthreaded half female member 213 of retainer 21, lug 233 is formed on second slider 23 so as to push the needle sideways and thereby facilitate easy removal of the needle from the holder.

After the used blood collection needle is removed from the holder, first slider 22 will be pushed toward retainer 21 so that slanted ends 226 urge hooks 224 inward. Thus, ends 226 advance over the frame's protrusions 243, which consequently snap in grooves 225 so that half female members 213 and 223 return to the "closed" position shown in FIGS. 3 and 5.

The holder described above can not only be used with a blood collection needle but also with any other appropriate medical tools such as syringes.

It will now be apparent that users of the holder for a blood collection needle of the invention need not touch the used needle when removing same. Thus, they are protected from erroneously pricking themselves with the needle which could infect them with serious diseases. The holder offers an economic advantage because it can be used with usual medical needles whose hubs are threaded. In the case where the hubs are threaded, they are firmly held in position such that they do not unintentionally slip off, shake, or rock. Thus, medical operations for taking blood samples are now rendered much safer by the holder provided herein.

What is claimed is:

1. The holder for a blood collection needle comprising:

a cylinder having an open proximal end, a distal end closed by an end wall, and an aperture formed in said end wall; and a needle fixing mechanism disposed at said distal end of said cylinder, said mechanism including a first slider, a second slider, a retainer, and a frame, said second slider and said retainer being disposed on said end wall, said first slider being disposed on said second slider, and said frame being affixed to said cylinder so as to hold said first slider, said second slider, and said retainer on said end wall, wherein said first slider and said retainer have half female members integrally formed thereon, said first slider is movable toward said second slider such that said mechanism is in a closed state in which said first slider engages said frame such that said half female members come together to define a complete female member, and said second slider is movable toward said first slider such that said mechanism is in an open state in which said first slider is disengaged from said frame.

* * * * *